(12) United States Patent
Glaw

(10) Patent No.: US 8,695,597 B2
(45) Date of Patent: Apr. 15, 2014

(54) PROCESS FOR OPERATING A RESPIRATOR AND/OR ANESTHESIA DEVICE IN THE APRV MODE WITH THE %PEF CRITERION AND A DEVICE OPERATED CORRESPONDINGLY

(75) Inventor: Tobias Glaw, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1634 days.

(21) Appl. No.: 12/131,277

(22) Filed: Jun. 2, 2008

(65) Prior Publication Data
US 2008/0295840 A1 Dec. 4, 2008

(30) Foreign Application Priority Data
Jun. 4, 2007 (DE) .......................... 10 2007 026 035

(51) Int. Cl.
*A62B 7/04* (2006.01)
*F16K 31/26* (2006.01)

(52) U.S. Cl.
USPC ............. 128/204.26; 128/204.18; 128/203.12

(58) Field of Classification Search
USPC ............. 128/203.12, 204.18, 204.21, 204.23, 128/204.26, 204.22, 200.24
See application file for complete search history.

(56) References Cited

U.S. PATENT DOCUMENTS

| | | | | |
|---|---|---|---|---|
| 4,211,221 A * | 7/1980 | Schwanbom et al. ... | 128/204.26 |
| 5,398,682 A * | 3/1995 | Lynn ........................... | 600/335 |
| 6,095,140 A * | 8/2000 | Poon et al. ............... | 128/204.26 |
| 6,158,433 A * | 12/2000 | Ong et al. ................ | 128/204.21 |
| 6,474,333 B1 * | 11/2002 | Heinonen ................ | 128/203.12 |
| 6,539,940 B2 * | 4/2003 | Zdrojkowski et al. ... | 128/204.23 |
| 6,655,382 B1 * | 12/2003 | Kolobow ................ | 128/204.25 |
| 6,752,151 B2 * | 6/2004 | Hill .......................... | 128/204.18 |
| 6,948,497 B2 * | 9/2005 | Zdrojkowski et al. ... | 128/204.18 |
| 7,013,892 B2 * | 3/2006 | Estes et al. .............. | 128/204.18 |
| 7,100,607 B2 * | 9/2006 | Zdrojkowski et al. ... | 128/204.18 |
| 7,246,618 B2 * | 7/2007 | Habashi .................. | 128/204.23 |
| 7,770,580 B2 * | 8/2010 | Kruger et al. ........... | 128/204.21 |
| 7,814,906 B2 * | 10/2010 | Moretti ................... | 128/204.23 |
| 7,891,353 B2 * | 2/2011 | Chalvignac ............. | 128/204.21 |
| 2005/0224078 A1 * | 10/2005 | Zdrojkowski et al. ... | 128/204.23 |
| 2006/0005834 A1 * | 1/2006 | Aylsworth et al. ...... | 128/204.21 |
| 2006/0174884 A1 * | 8/2006 | Habashi .................. | 128/204.21 |
| 2007/0000491 A1 * | 1/2007 | Chalvignac ............. | 128/204.23 |
| 2007/0044796 A1 * | 3/2007 | Zdrojkowski et al. ... | 128/204.18 |
| 2008/0072901 A1 * | 3/2008 | Habashi .................. | 128/204.18 |
| 2008/0078392 A1 * | 4/2008 | Pelletier et al. .......... | 128/204.23 |
| 2008/0087284 A1 * | 4/2008 | Krueger et al. .......... | 128/204.21 |
| 2008/0283060 A1 * | 11/2008 | Bassin ..................... | 128/204.18 |
| 2008/0295839 A1 * | 12/2008 | Habashi .................. | 128/204.22 |
| 2009/0114222 A1 * | 5/2009 | Ralfs et al. .............. | 128/204.23 |
| 2009/0293876 A1 * | 12/2009 | Soliman et al. .......... | 128/204.22 |
| 2010/0224189 A1 * | 9/2010 | Lorenzen et al. ........ | 128/204.21 |
| 2011/0139153 A1 * | 6/2011 | Chalvignac ............. | 128/204.21 |
| 2011/0240021 A1 * | 10/2011 | Eger et al. ................ | 128/203.14 |

* cited by examiner

*Primary Examiner* — Jackie Ho
*Assistant Examiner* — Aundria Hairell
(74) *Attorney, Agent, or Firm* — McGlew and Tuttle, P.C.

(57) ABSTRACT

A process for operating a respirator and/or anesthesia device in the APRV mode with the % PEF criterion which includes a detection of a spontaneous expiratory effort by the patient and initiation of a pressure release phase when the detected spontaneous expiratory effort by the patient falls within a predetermined trigger window ($Tf_{reg}$). A device is provided that is operated correspondingly.

17 Claims, 4 Drawing Sheets

US 8,695,597 B2

PROCESS FOR OPERATING A RESPIRATOR AND/OR ANESTHESIA DEVICE IN THE APRV MODE WITH THE %PEF CRITERION AND A DEVICE OPERATED CORRESPONDINGLY

CROSS REFERENCE TO RELATED APPLICATIONS

This application claims the benefit of priority under 35 U.S.C. §119 of German Patent Application DE 10 2007 026 035.2 filed Jun. 4, 2007, the entire contents of which are incorporated herein by reference.

FIELD OF THE INVENTION

The present invention pertains to a process for operating a respirator (also known as ventilator) and/or anesthesia device in the APRV (Airway Pressure Release Ventilation) mode with the % PEF (Peak Expiratory Flow) criterion. The present invention pertains furthermore to a respirator and/or anesthesia device for respirating (also known as ventilating) a patient in the APRV mode with the % PEF criterion.

BACKGROUND OF THE INVENTION

A respiration mode APRV (Airway Pressure Release Ventilation), which is, similarly to the CPAP mode, a mode with a continuous positive airway pressure (CPAP), is known from practice. Contrary to the CPAP respiration mode, an upper pressure $P_{high}$ is set in the APRV mode. This pressure $P_{high}$ is regularly lowered for a short duration each time to a lower pressure level $P_{low}$, this pressure reduction being called "pressure release." The patient being respirated by means of APRV can breathe spontaneously at any time, but the pressure release is not synchronized with the patient's respiratory activity. It is typical of the APRV mode that a duration $T_{high}$, during which the pressure $P_{high}$ is applied, is usually longer than a duration $T_{low}$, during which the lower pressure $P_{low}$ is present. FIGS. 1A and 1B show an example of a respiration in the APRV mode in a simulation.

During respiration in the APRV mode, the mean respiration pressure is maintained at a comparatively high level, which leads to improved oxygenation. The elimination of $CO_2$ is supported by the pressure release. Due to the short duration $T_{low}$ and the short duration of the pressure release, removal of air from the lungs to the extent that alveoli could collapse and could not participate in the ventilation any longer is prevented from occurring. The duration $T_{low}$ is set such that complete breathing out is prevented from occurring. It can be recognized from FIG. 1B that the pressure release is terminated before the patient flow has risen to 0 L/minute (see the times t=5.5 sec; t=13 sec; t=21.5 sec in FIG. 1B).

A new set value for APRV ventilation, which is circumscribed as "optimal flow termination based on a percentage of peak expiratory flow," is proposed in the patent application US 2006/0174884 A1 of Nader M. Habashi. This set value will hereinafter be called % PEF (Peak Expiratory Flow). The parameter % PEF is set in percentage of a maximum expiratory flow PEF. The pressure release is terminated when the instantaneous expiratory flow of the patient relative to the maximum expiration flow has dropped below the percentage set as % PEF (cf. FIG. 2). As a result, the algorithm automatically adapts the duration of pressure release to changes in the lungs.

However, respiration in the APRV respiration mode with the % PEF criterion, as it is described in the above-mentioned US 2006/0174884 A1, has the following problem: since the APRV mode is not synchronized with the patient, the patient can breathe spontaneously at any time, i.e., even during the pressure release phase. Due to such a spontaneous respiratory effort, the patient can generate a stronger inspiratory flow, above all in case of smaller pressure differences between $P_{high}$ and $P_{low}$, than the expiratory flow generated by the respirator. As a consequence of this, a positive (inspiratory) patient flow prevails instead of the expected expiratory flow, and the % PEF criterion cannot therefore be met or it will be met at a markedly later point in time only, namely, when the spontaneous inspiration of the patient again passes over into an expiration. Until the set % PEF criterion is met during the latter expiration, the respirator applies the low pressure $P_{low}$ over an undesirably long time period. A safety means may be provided for interrupting the expiration after the end of a set maximum duration $T_{low}$. However, this is a safety means, which cannot prevent an excessive removal of air from the lungs with the above-described problems and risks during the prolonged expiration time.

SUMMARY OF THE INVENTION

The object of the present invention is therefore to provide an improved process for operating a respirator and/or anesthesia device in the APRV mode with the % PEF criterion. Another object of the present invention is to propose a suitable respirator and/or anesthesia device.

The process according to the present invention comprises the detection of a spontaneous expiratory effort of the patient, the patient being able to be either a human being or an animal. Such a spontaneous expiratory effort can be recognized, for example, in connection with a monitoring of the patient flow. Technical possibilities therefor are well known to the person skilled in the art. However, since not every recognized, spontaneous expiration by the patient shall trigger a pressure release phase, it is proposed according to the present invention that a pressure release phase (a pressure release for short) will be initiated when the detected, spontaneous expiratory effort of the patient falls within a predetermined trigger window. This trigger window corresponds to a duration which begins, for example, at the end of the inspiration (corresponding to the phase with the pressure $P_{high}$) and before the end of the inspiration time. If a spontaneous expiration is recognized in this trigger window, which is a time window, a pressure release is triggered, and a pressure release will otherwise begin regularly at the end of the trigger window and hence after the end of the inspiration time.

It is advantageously ensured in this manner according to the present invention that a pressure release cannot take place during a phase of the respiration cycle in which a spontaneous inspiration by the patient leads to the drawbacks mentioned above in the discussion of the state of the art. The process according to the present invention thus makes possible a very good synchronization between respiration in the APRV mode with the % PEF criterion and the allowing of spontaneous inspiration by the patient.

Thus, it is provided in accordance with a preferred embodiment of the process according to the present invention that the process comprises the setting of the trigger window. "Setting" comprises here both the fixing of the duration of the trigger window and of the position of that window within the respiration cycle. An especially good synchronization can thus be achieved without additional requirements imposed on the process or the system when the trigger window is set to be larger than the cycle time of the patient (spontaneous inspiration and expiration). In addition, it is advantageous to open the trigger window by the end of the inspiration time such that even a pressure release initiated too early at the beginning of the trigger window will still allow a sufficient inspiration time for the patient, which may have a favorable effect on the patient's oxygen supply.

The fixing of the trigger window may also be defined according to the present invention as the fixing of the conditions on the detected, spontaneous expiratory effort by the patient, based on which a pressure release is initiated within the trigger window. Thus, provisions may be made for triggering a pressure release not only at the start of a spontaneous expiration within the trigger window, but also when a spontaneous expiration, whose start is outside the trigger window and before the beginning of that window in time, is recognized. In other words, a spontaneous expiratory effort by the patient does not have to begin within the trigger window when the general conditions of the trigger window are set correspondingly. An advantage associated herewith is that the minimum requirement on the duration of the trigger window can be advantageously shortened in this manner. This contributes to the granting of a longer inspiration time with the above-described advantageous effects for oxygenation.

Another preferred embodiment of the process according to the present invention comprises the initiation of the pressure release phase when a patient flow within the trigger window is smaller than a predetermined value. If the patient flow assumes a value below, for example, 1 L/minute after opening or beginning of the trigger window, pressure release is started or initiated. This makes it possible to initiate the pressure release not only during the spontaneous expiration by the patient, but even during the inspiratory pause and/or the expiratory pause of the patient. This process advantageously enables the respirator and/or anesthesia device (respirator for short) to start a pressure release within the greatest possible period of the respiration cycle, while the criterion of synchronization, namely, the fact that a pressure release is prevented from coinciding with the spontaneous inspiratory effort by the patient, is still met.

Another preferred embodiment of the process according to the present invention comprises the prolongation of the inspiration time ($T_{high}$) of a respiration cycle beyond a preset inspiration time ($T_{high}$) by the duration by which a pressure release phase had occurred in a preceding inspiration phase before the end of the inspiration phase.

The percentage of the preset inspiration time ($T_{high}$) of the inspiration phase terminated prematurely by the pressure release, which percentage was not available for an inspiration, is thus utilized to prolong an inspiration time, which will occur later in time. This advantageously ensures that the inspiration time is, on average, constant and can lead to better oxygenation.

Yet another preferred embodiment of the process according to the present invention comprises the shifting of the start of the trigger window to a point in time after the end of both a minimum inspiration time and after the end of a compensatory period. This process step also ensures the maintenance of an inspiration time that is constant, on average, and is used to improve the oxygenation compared to the case in which the prolongation of an inspiration time of a respiration cycle would be prematurely interrupted again by a pressure release to compensate a pressure release of a preceding inspiration, which was triggered in the trigger window, and the necessary mean inspiration time could not be available to the patient.

This object is also accomplished by the anesthesia device and/or respirator for respirating a patient in the APRV mode with the % PEF criterion which includes a means for detecting a spontaneous expiratory effort by the patient and a means for determining whether the spontaneous expiratory effort falls within a predetermined trigger window (time window). Advantageous variants of the anesthesia device and/or respirator according to the present invention are also provided by further particulars described herein. Since all the advantages discussed above can be achieved to the full extent by means of the anesthesia device and/or respirator according to the present invention, reference is explicitly made to the above discussion of these advantages to avoid repetition. A device with means for carrying out the process according to the present invention is thus proposed according to the present invention.

The present invention will be explained in detail on the basis of an example with reference to the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1A:
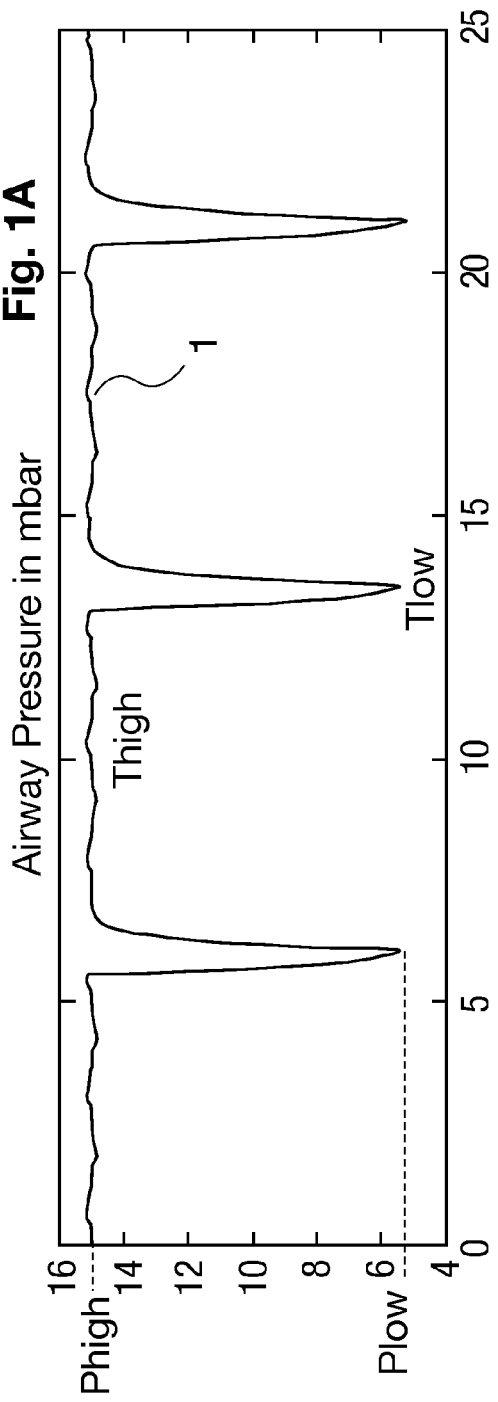
FIG. 1A is a graph with airway pressure in mbar versus time in seconds showing simulation of respiration in the APRV mode.
Figure 1B:
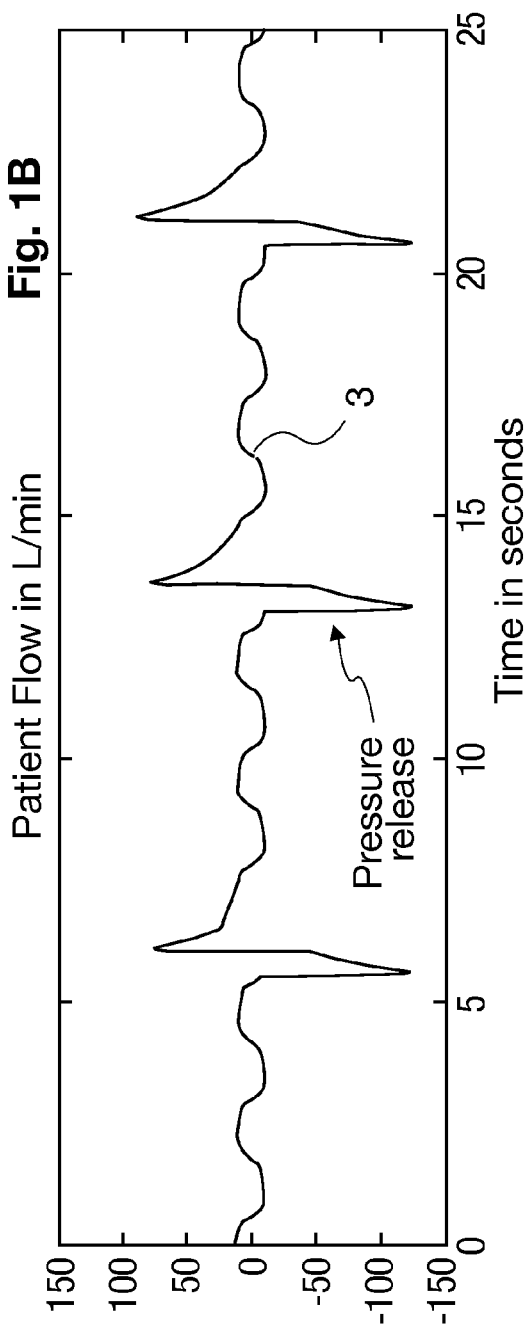
FIG. 1B is a graph with patient flow in L/minute versus time in seconds showing simulation of respiration in the APRV mode.

Referring to the drawings in particular, FIGS. 1A and 1B show an example of respiration in the APRV mode in a simulation, where FIG. 1A shows an airway pressure 1 in mbar, and FIG. 1B shows the corresponding patient flow 3 in L/minute, each over time. The airway pressure 1 varies here between an upper pressure level $P_{high}$ during a high pressure period and a lower pressure level $P_{low}$ during a low pressure period. The pressure level $P_{high}$ is applied for this over a duration $T_{high}$, and the lower pressure level $P_{low}$ over a duration $T_{low}$. One of three pressure release phases shown is marked with an arrow in the lower view in FIG. 1B.

Figure 2:
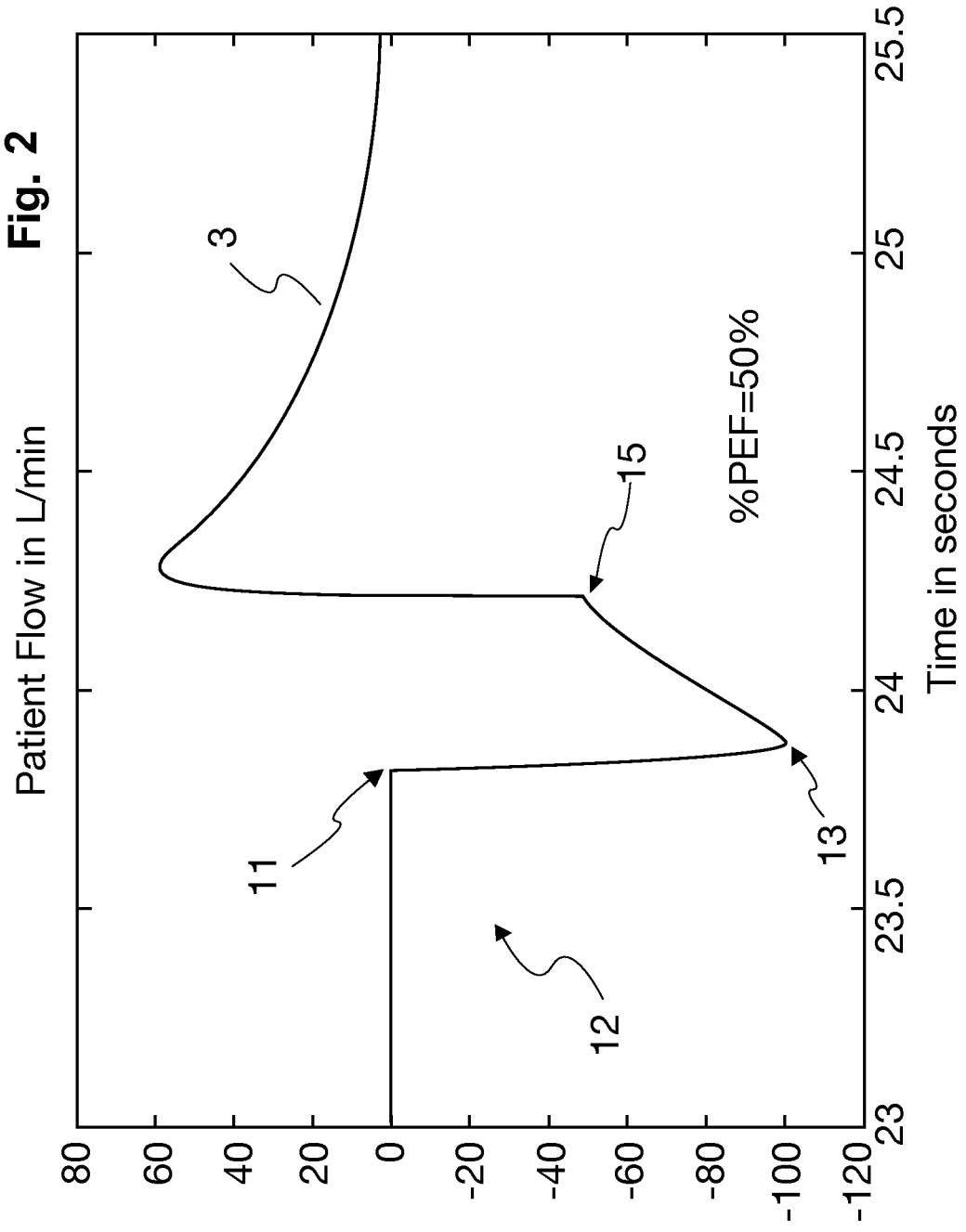
FIG. 2 is a graph with patient flow in L/minute versus time in seconds showing a respiration scheme in the APRV mode with a % PEF criterion.

FIG. 2 shows the patient flow 3 over time in a simulation of an APRV respiration. FIG. 2 shows a point in time 11 at which a pressure release phase 12 is started. FIG. 2 shows, furthermore, a point in time 13, at which a maximum flow—equaling 100 L/minute in this case—is reached. In addition, a point in time 15, at which the pressure release phase 12 is interrupted at a set % PEF of 50%, is marked in FIG. 2.

Figure 3:
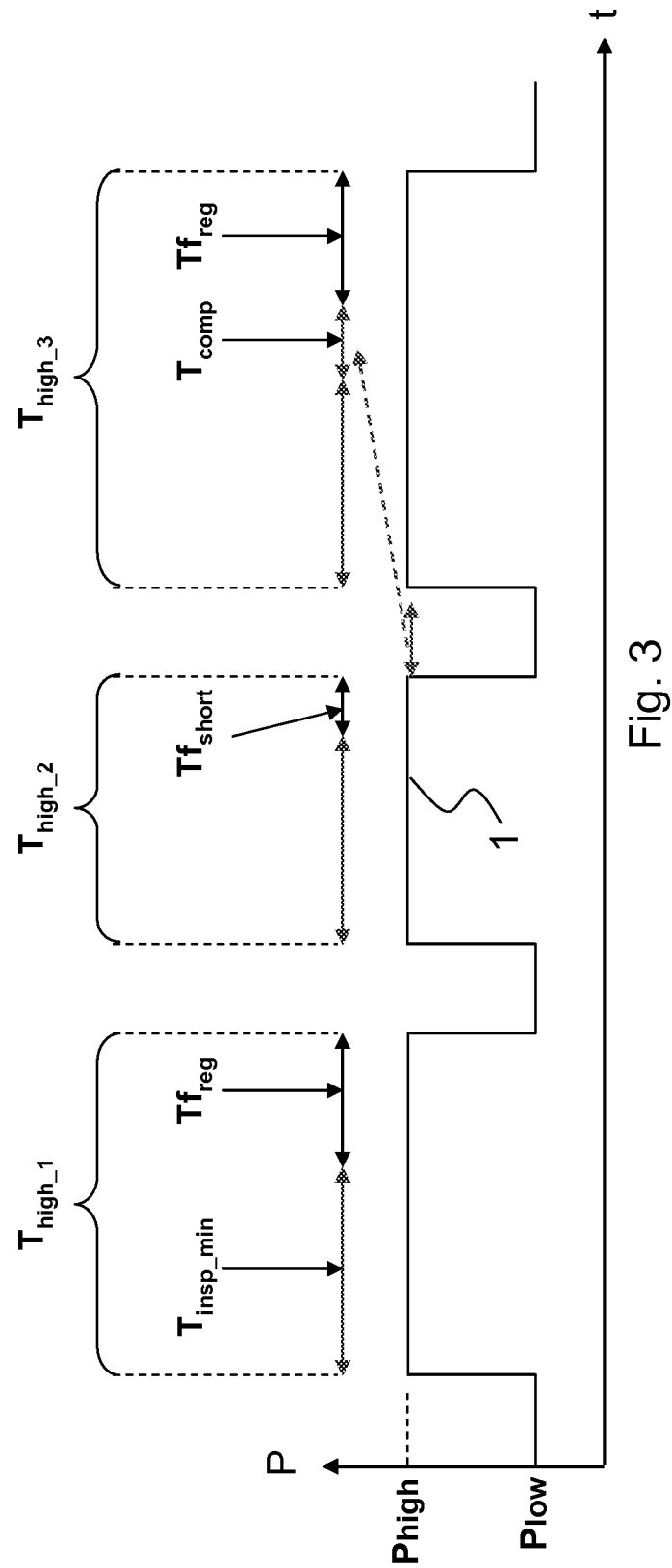
FIG. 3 is a graphical representation showing variable duration of the inspiration time in case of the use of an embodiment according to the present invention of the process according to the present invention.

FIG. 3 shows a variable duration of the inspiration time in case of the use of the embodiment according to the process of the present invention. Thus, FIG. 3 shows a first inspiration time $T_{high\_1}$. It is composed of a preset, constant, minimum inspiration or high pressure time $T_{insp\_min}$, which is contained in the inspiration times $T_{high\_1}$, $T_{high\_2}$, $T_{high\_3}$ shown in FIG. 3, and which equals 75% of the duration of $T_{high\_1}$ in the example shown in FIG. 3, and a trigger window $Tf_{reg}$, which accounts for 25% of the first inspiration time $T_{high\_1}$ here and opens after the end of the minimum inspiration time $T_{insp\_min}$. The pressure release is triggered at the latest after the end of the regular trigger time $Tf_{reg}$.

The second inspiration time $T_{high\_2}$ shown in FIG. 3 is composed, in turn, of the minimum inspiration time $T_{insp\_min}$ and a trigger window. This trigger window $Tf_{short}$ is, however, shortened compared to the regular trigger window $Tf_{reg}$ because of spontaneous expiratory efforts by the patient, which are not shown, or because the patient flow has dropped below a set minimum, as was described above. It can be clearly recognized from FIG. 3 that the total inspiration time $T_{high\_2}$ is shorter than the first inspiration time $T_{high\_1}$ because of the shortened trigger window.

The third inspiration time $T_{high\_3}$ shown in FIG. 3 is prolonged by a duration $T_{comp}$ to compensate the shortening of the total inspiration time available to the patient due to the shortening of the inspiration time $T_{high\_2}$. The total duration of the inspiration time $T_{high\_3}$ is therefore composed of the inspiration time $T_{insp\_min}$, the regular trigger time $Tf_{reg}$ and the duration $T_{comp}$. The trigger window thus opens only after the end of the inspiration time $T_{insp\_min}$ and the duration $T_{comp}$.

Figure 4:
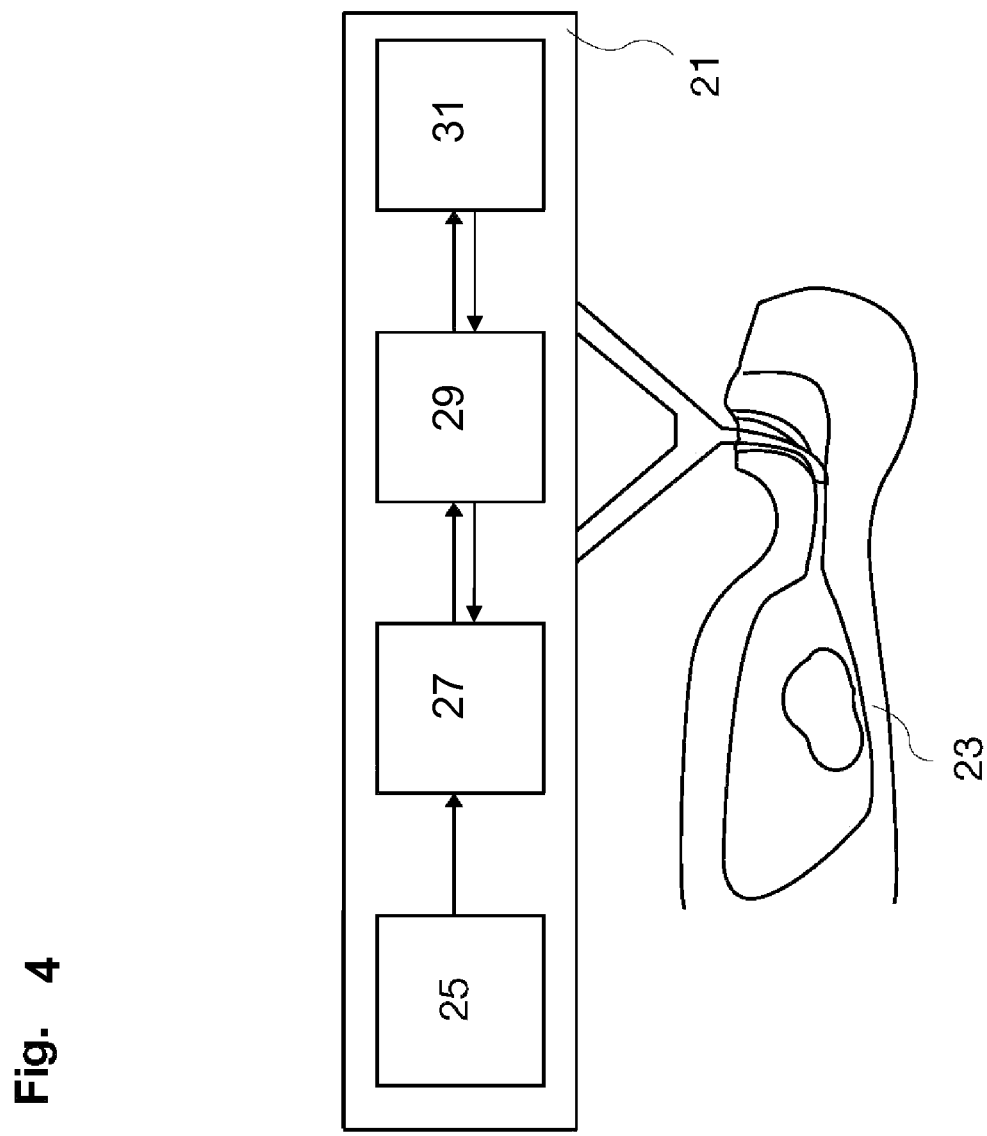
FIG. 4 is a simplified exemplary view of a respirator according to the present invention.

FIG. 4 shows a schematically simplified respirator and/or anesthesia device 21 according to the present invention for respirating a patient 23. The device 21 has a means 25 for fixing the trigger window within the inspiration time, a means 27 for determining whether the spontaneous expiratory effort falls within a predetermined trigger window, and a means 29 for detecting a spontaneous expiratory effort by the patient 23. The device 21 has, moreover, a means 31 for initiating the pressure release when a patient flow in the trigger window is smaller than a predetermined value or a spontaneous expiratory effort is recognized.

Thus, the present invention proposes, for the first time ever, a process for operating a respirator and/or anesthesia device in the APRV mode with the % PEF criterion with the steps: detection of a spontaneous expiratory effort by the patient and initiation of a pressure release phase when the detected spontaneous expiratory effort by the patient falls within a predetermined trigger window. The present invention proposes, moreover, a device operated correspondingly.

While specific embodiments of the invention have been shown and described in detail to illustrate the application of the principles of the invention, it will be understood that the invention may be embodied otherwise without departing from such principles.

What is claimed is:

1. A process for operating a respirator and/or anesthesia device in Airway Pressure Release Ventilation (APRV) mode with a % Peak Expiratory Flow (PEF) criterion, the process comprising the steps of:
    providing a respirator and/or anesthesia device;
    flowing breathing gases to a patient using said respirator and/or anesthesia device in the Airway Pressure Release Ventilation (APRV) mode with an airway pressure varied between an upper pressure level during a high pressure period and a lower pressure level during a pressure release phase;
    detecting a spontaneous expiratory effort by a patient;
    switching said flowing of the breathing gas using said respirator and/or anesthesia device from said high pressure period to said pressure release phase when the detected spontaneous expiratory effort by the patient falls within a predetermined trigger window,
    switching said flowing of the breathing gas using said respirator and/or anesthesia device from said pressure release phase to said high pressure period when an instantaneous patient expiratory flow relative to a maximum expiration flow has dropped below a set percentage;
    setting a length of said trigger window;
    determining a minimum inspiration time of a respiration cycle;
    prolonging an inspiration time of a subsequent respiration cycle beyond said minimum inspiration time by a duration by which said trigger window was shortened in a preceding inspiration phase because of said pressure release phase occurring before the end of that trigger window.

2. A process in accordance with claim 1, further comprising the step of:
    fixing said trigger window.

3. A process in accordance with claim 1, wherein said step of switching to said pressure release phase occurs when a patient flow within said trigger window is smaller than a predetermined value or when the spontaneous expiratory effort is detected.

4. A process in accordance with claim 1, further comprising the step of:
    shifting a start of said trigger window to a point in time after an end of said minimum inspiration time and after an end of said duration.

5. A process for operating a respirator and/or anesthesia device the process comprising the steps of:
    providing a respirator and/or anesthesia device;
    flowing breathing gases for providing respiration to a patient using said respirator and/or anesthesia device in Airway Pressure Release Ventilation (APRV) mode with an airway pressure varied between an upper pressure level and a lower pressure level with the lower pressure level comprising a pressure release phase;
    switching said flowing of the breathing gas using said respirator and/or anesthesia device from the pressure release phase with a return to the upper pressure level when an instantaneous patient expiratory flow relative to a maximum expiration flow has dropped below a set percentage;
    detecting a spontaneous expiratory effort by a patient;
    switching said flowing of the breathing gas using said respirator and/or anesthesia device to the pressure release phase when the detected spontaneous expiratory effort by the patient falls within a predetermined trigger window or otherwise initializing the pressure release phase at the end of said predetermined trigger window;
    setting a length of said trigger window;
    determining a minimum inspiration time of a respiration cycle;
    prolonging an inspiration time of a subsequent respiration cycle beyond said minimum inspiration time by a duration by which said trigger window was shortened in a preceding inspiration phase because of said pressure release phase occurring before the end of that trigger window.

6. A process in accordance with claim 5, wherein said step of switching to the pressure release phase occurs when a patient flow within said trigger window is smaller than a predetermined value or when the spontaneous expiratory effort is detected.

7. A process in accordance with claim 5, further comprising the step of:

shifting a start of said trigger window to a point in time after an end of said minimum inspiration time and after an end of said duration.

8. A process in accordance with claim 5, further comprising:
maintaining said upper pressure level for a predetermined minimum inspiration time after said expiratory flow has dropped below said percentage, said trigger window occurring after said minimum inspiration time.

9. A process in accordance with claim 8, further comprising:
varying the airway pressure between a plurality of said upper pressure levels and said lower pressure levels;
ending a first of said plurality of said upper pressure levels before an expiration of said trigger window because of the detected spontaneous expiratory effort by the patient;
prolonging said upper pressure level in a subsequent second upper pressure level when a previous upper pressure level has ended before said expiration of said trigger window because of detected spontaneous expiratory effort by the patient.

10. A process in accordance with claim 9, wherein:
said upper pressure level in said subsequent second upper pressure level is prolonged by an amount that said trigger window has been shortened in said previous upper pressure level because of the detected spontaneous expiratory effort by the patient.

11. A process in accordance with claim 1, further comprising:
maintaining said high pressure period for a predetermined minimum inspiration time after said expiratory flow has dropped below said percentage, said trigger window occurring after said minimum inspiration time.

12. A process in accordance with claim 11, further comprising:
varying an airway pressure between a plurality of said upper pressure levels and a plurality of pressure release phases;
ending a first of said plurality of said upper pressure levels before an expiration of said trigger window because of the detected spontaneous expiratory effort by the patient;
prolonging said upper pressure level in a subsequent second upper pressure level when a previous upper pressure level has ended before said expiration of said trigger window because of detected spontaneous expiratory effort by the patient.

13. A process in accordance with claim 12, wherein:
said upper pressure level in said subsequent second upper pressure level is prolonged by an amount that said trigger window has been shortened in said previous upper pressure level because of the detected spontaneous expiratory effort by the patient.

14. A process for ventilating a patient, the process comprising the steps of:
providing a respirator and/or anesthesia device;
flowing breathing gases to a patient using said respirator and/or anesthesia device in Airway Pressure Release Ventilation (APRV) mode with an airway pressure varied between an upper pressure level during a high pressure period and a lower pressure level during a low pressure period;
measuring an expiration flow from the patient during said low pressure period;
determining a maximum expiration flow during said low pressure period;
switching said flowing of the breathing gas using said respirator and/or anesthesia device from said low pressure period to said high pressure period when a present expiration flow is below a predetermined percentage of the maximum expiration flow;
dividing said high pressure period into a minimum high pressure time and a trigger window, said trigger window occurring after said minimum high pressure time;
detecting a spontaneous expiratory effort by a patient during said high pressure period;
switching said flowing of the breathing gas using said respirator and/or anesthesia device from said high pressure period to said low pressure period at the earlier of, when the detected spontaneous expiratory effort by the patient falls within said trigger window, or an end of said trigger window;
varying the airway pressure between a plurality of said high pressure periods and a plurality of said low pressure periods;
ending one of said plurality of high pressure periods before an expiration of said trigger window because of detected spontaneous expiratory effort by the patient;
prolonging said minimum high pressure time in a subsequent high pressure period when a previous high pressure period has ended before said expiration of said trigger window because of the detected spontaneous expiratory effort by the patient.

15. A process in accordance with claim 14, further comprising:
maintaining said high pressure period after said expiratory flow has dropped below said percentage when the spontaneous expiratory effort occurs during said minimum high pressure time.

16. A process in accordance with claim 14, wherein:
said minimum high pressure time in said subsequent high pressure period is prolonged by an amount that said trigger window had been shortened in said previous high pressure period because of the detected spontaneous expiratory effort by the patient.

17. A process in accordance with claim 14, further comprising:
maintaining said high pressure period when the spontaneous expiratory effort occurs during said minimum high pressure time.

* * * * *